United States Patent [19]

Titmas

[11] Patent Number: 5,711,817
[45] Date of Patent: Jan. 27, 1998

[54] METHOD FOR THE CONTINUOUS CONVERSION OF CELLULOSIC MATERIAL TO SUGAR

[75] Inventor: James A. Titmas, Fairlawn, Ohio

[73] Assignee: Eau-Viron Incorporated, Hudson, Ohio

[21] Appl. No.: 644,401

[22] Filed: May 1, 1996

[51] Int. Cl.$^6$ .................................................. C13K 1/02
[52] U.S. Cl. .................................. 127/37; 127/38; 127/43; 127/1; 435/161
[58] Field of Search .................................. 127/37, 38, 36, 127/43, 1; 162/25, 81; 435/162, 283.1, 161, 163, 165, 289.1, 293.1, 295.1, 295.2; 422/129, 242, 184.1; 210/741, 757, 761, 766; 166/244.1, 250.01, 300, 302, 303

[56] References Cited

U.S. PATENT DOCUMENTS

| | | | |
|---|---|---|---|
| 3,449,247 | 6/1969 | Bauer | 210/63 |
| 3,464,885 | 9/1969 | Land et al. | 210/17 |
| 3,853,759 | 12/1974 | Titmas | . |
| 4,272,383 | 6/1981 | McGrew | 210/741 |
| 4,792,408 | 12/1988 | Titmas | 210/747 |
| 5,135,861 | 8/1992 | Pavilon | 435/162 |
| 5,160,581 | 11/1992 | Titmas | 162/61 |

FOREIGN PATENT DOCUMENTS

| | | | |
|---|---|---|---|
| 27 44 067 | 4/1979 | Germany | 127/37 |

OTHER PUBLICATIONS

"A review of developments in the acid hydrolysis of cellulosic wastes" by Anderson et al. *Proc Instn Mech Engrs* vol. 201 No. C2, pp. 117–123 (1987).

"An Evaluation of Hydrolysis Technology for the Conversion of Cellulosic Feedstocks to Ethanol and Other Chemicals" by Moore–Bulls et al., Presented at Seventh Canadian Bioenergy R&D Seminar, Ottawa, Ontario, 9 pages (Apr. 1989).

"An improved process for converting cellulose to ethanol" by Goldstein et al., *Tappi Journal*, pp. 135–140 (Aug. 1992).

TVA "Biomass Research Program Update" vol. 2, No. 1, 2 pages (Nov. 1989).

TVA "Biomas Research Program Update" vol. 3, No. 1, 2 pages (Oct. 1990).

TVA "Biomass Research Program Update" vol. 4, No. 1, 2 pages (May 1991).

"Comparison of MSW Utilization Technologies—Ethanol Production, RDF Combustion, and Mass Burning" by Bulls et al., Presented at the Southern Biomass Conference, Baton Rouge, Louisiana, pp. cover–12 (Jan. 1991).

"Ethanol Production from Refuse–Derived Waste Using Dilute Sulfuric Acid Hydrolysis" by Barrier et al., National Bioenergy Conference, Coeur d'Alene, Idaho, 10 pages (Mar. 1991).

"Feedstock Availability of Biomass and Wastes" by Barrier et al., Included in the ACS Symposium Book Series *Emerging Materials and Chemicals from Biomass*, cover–12 (Mar. 1991).

"Continuous Acid Hydrolysis of Cellulosic Biomass for Production of Xylose, Glucose and Furfural", by Grethlein et al. *Food, Feed and Feul from Biomass*, Chapter VIII, part A1, 22 pages, No Date Provided.

"Continuous Acid Hydrolysis of Lignocelluloses for Production of Xylose, Glucose and Furfural" by Grethlein et al., *Food, Feed and Fuel*, Chapter 16, pp. 268–279 No Date Provided.

"Glucose Decomposition at High Temperature, Mild Acid, and Short Residence Times" Smith et al., 22 pages, Sol. Energy (1982).

"Industrial Pyrolysis of Cellulosic Materials", by Shafizadeh, *Applied Polymer Symposium*, No. 28, pp. 153–174 (1975).

"Kinetics of Acid Hydrolysis of Corn Stover" by McParland et al., 20 pages Solar Energy (1982).

"Kinetics of Dilute Acid Hydrolysis of Cellulose Originating from Municipal Solid Wastes" by Malester et al., *Ind. Eng. Chem. Res.* vol. 31, No. 8, pp. 1998–2003 (1992).

"Kinetics of the Acid Hydrolysis of Cellulose Found in Paper Refuse" by Eagan et al., *Environmental Science & Technology* vol. 5, No. 3 pages (1971).

"Potential Contribution of Furfural to the Economics of Ethanol Production from Hardwoods" by Barrier et al., Presented at the Southern Biomass Conference, Virginia Polytechnic Institute and State University, pp. cover–14 (Sep. 1989).

"Thermal Behavior of Carbohydrates" by Shafizadeh, *J. Polymer Sci: Part C* No. 36, pp. 21–51 (1971).

"Wastepaper as a Feedstock for Ethanol Production" by Bergeron et al., National Renewable Energy Laboratory, 28 pages (Nov. 1991).

*Primary Examiner*—William H. Beisner
*Attorney, Agent, or Firm*—Renner, Kenner, Greive, Bobak, Taylor & Weber

[57] ABSTRACT

Cellulosic material is converted to ethanol by hydrolyzing the cellulosic material in a gravity pressure vessel (50), and fermenting the product thereof. The gravity pressure vessel (50) employed is adapted to accommodate a continuous hydrolysis reaction and maximize the fermentable product yield on a commercial scale. The gravity pressure vessel (50) employed is also adapted to maximize the thermodynamic efficiencies of the hydrolysis reaction, as well as the entire ethanol producing process.

4 Claims, 6 Drawing Sheets

METHOD FOR THE CONTINUOUS CONVERSION OF CELLULOSIC MATERIAL TO SUGAR

TECHNICAL FIELD

The present invention is generally directed toward a process whereby cellulosic material is converted to ethanol. Specifically, the present invention is directed toward an apparatus and method for the hydrolysis of cellulosic material to sugars which may be subsequently fermented. More specifically, the present invention is directed to an apparatus and method for the conversion of cellulosic material suspended in a fluid mixture via acid hydrolysis in a gravity pressure vessel.

BACKGROUND ART

Ethanol is a viable, economical, and relatively clean fuel substitute or additive. It is easily obtained from the fermentation of grain or other substances containing sugars and starches. Although grain and other sugar-bearing substances are in abundance, the conversion of cellulosic material, such as found in municipal solid waste, to sugar followed by the fermentation of the sugar has been found useful for the purpose of obtaining ethanol. The use of such waste cellulose has been particularly attractive in the face of higher grain costs and concerns about waste disposal.

Cellulosic material generally includes waste paper, agricultural chafe, municipal solid waste residual fluff, and wood products. These substances are converted to sugar via hydrolysis. Heretofore in the art, cellulosic material has been hydrolyzed by first reducing the material to a pulp and reacting that pulp with sulfuric acid. Upon the introduction of heat, hydrolysis begins and the cellulosic material is converted to sugar. The reaction is quenched by rapid cooling of the mixture, followed by acid neutralization. Rapid quenching is necessary because the hydrolysis reaction is virtually instantaneous, and over exposure to heat and acidic conditions will result in the decomposition of the sugar product thereby reducing yield.

This process, however, is thermally inefficient because the heat introduced to the system is lost through the rapid cooling of the system. Furthermore, inefficiencies resulting from the use of thick pulp solutions of cellulosic material, which conventionally contains approximately 20% suspended solids, have been recognized. Specifically, these solutions require screw augers to accomplish the required mixing of acid and heat. Thus, when a reaction vessel is 1,000 cubic feet, which is the minimum for commercial quantities, the time to achieve uniform mixing can be as long as twenty minutes. In addition to the inefficiencies associated with powering the auger, this process will result in poor sugar yields as the time required to uniformly mix the pulp is typically too long, resulting in the decomposition of the resulting sugar.

Although the problems associated with the use of thick pulps can be overcome by simple dilution with water, the added energy required to handle such liquid results in further inefficiencies. Indeed, the total energy required to produce ethanol via such a process is greater than the heat of combustion of the resulting ethanol.

Thus, a need exists to convert cellulosic material to sugar for the purpose of obtaining ethanol in an efficient manner. Specifically, to create an economical fuel substitute or additive, the thermal and chemical inefficiencies associated with the processes of hydrolysis described hereinabove must be overcome.

Numerous methods and reactions for carrying out hydrolysis are known in the art. For example, Titmas in U.S. Pat. Nos. 3,853,759 and 4,792,408 discloses a continuously flowing hydraulic column wherein materials suspended in water are heated and gravity pressurized to effect hydrolysis. The heated material is forced upward by column pressure and thereby cooled and depressurized. Although this process could handle large quantities of cellulosic material, poor net sugar yield would be obtained because there is no means to control or manipulate the length of the hydrolysis reaction, nor is there any means to abruptly and specifically control the quenching of the reaction. To achieve satisfactory sugar yields, the hydrolysis reaction must be stopped part way through the normal coarse of chemical events. This has not been accomplished heretofore in the art.

Also, Pavilon, U.S. Pat. No. 5,135,861, discloses a method of producing ethanol from an aqueous slurry of biomass. The carbon dioxide resulting from fermentation is captured and used to catalyze the hydrolysis of the biomass. Pavilon, however, fails to efficiently utilize the heat needed for hydrolysis to catalyze further hydrolysis reactions, and thus the energy needed to convert the biomass to ethanol is greater than the resulting heat of combustion of the ethanol.

Thus, there remains a need for a method and apparatus for the conversion of cellulosic material to ethanol. Specifically, there remains a need for a method and apparatus for the efficient hydrolysis of cellulosic materials which includes improving sugar yield and capturing the heat needed for hydrolysis to further additional hydrolysis which will in turn result in a process that is both cost effective and thermodynamically efficient.

DISCLOSURE OF THE INVENTION

It is therefore a primary object of the present invention to provide a method for the hydrolysis of cellulosic material to sugar.

It is a further object of the present invention to provide a method for the hydrolysis of cellulosic material, as above, that has improved chemical and thermal efficiency.

It is still a further object of the present invention to provide a method for the hydrolysis of cellulosic material, as above, that is continuous and capable of hydrolyzing large volumes of cellulosic materials.

It is a further object of the present invention to provide a method for the hydrolysis of cellulosic material, as above, whereby a significant portion of the fluid temperature is internally recovered.

It is another object of the present invention to provide an apparatus for the hydrolysis of cellulosic materials.

It is yet another object of the present invention to provide an apparatus, as above, that efficiently recovers and utilizes the heat needed for hydrolysis to initiate further hydrolysis reactions.

It is still another object of the present invention to provide an apparatus, as above, that effectively provides for a predetermined reaction time and acidity level so as to maximize sugar yield.

At least one or more of the foregoing objects of the present invention together with the advantages thereof over existing methods and apparatus for hydrolyzing cellulosic materials, which shall become apparent from the specification which follows, are accomplished by the invention as hereinafter described and claimed.

In general, the present invention provides a method of hydrolyzing cellulosic material including the steps of processing the cellulosic material into a liquid stream, feeding the liquid stream to the top of a hydraulic downdraft column, conducting the liquid stream from the bottom of the hydraulic downdraft column into a reaction area, heating the liquid stream and lowering the pH of the liquid stream within the reaction area, thereby hydrolyzing the cellulosic material to form sugar within the liquid stream, and conducting the liquid stream containing the sugar from the reaction chamber to the top of a hydraulic updraft column.

The present invention further provides a method of converting cellulosic material to ethanol including the steps of processing the cellulosic material into a liquid stream, reacting the liquid stream within a gravity pressure vessel thereby converting the cellulosic material to sugar, and fermenting the sugar thereby forming ethanol.

The present invention also provides an apparatus for hydrolyzing cellulosic material within a continuous liquid stream which includes a first vertical passageway for receiving the liquid stream near the top thereof. A reaction area communicates with the first vertical passageway for receiving the liquid stream near the bottom of the first vertical passageway. Means are provided for delivering a gaseous material to the liquid stream, and in addition, means are provided for delivering heat to the liquid stream. A second vertical passageway communicates with the reaction area and receiving the liquid stream near the bottom thereof and delivers the liquid stream near the top thereof.

A preferred exemplary apparatus and method for the continuous conversion of cellulosic material to ethanol, which incorporates the concepts of the present invention, is shown by way of example in the accompanying drawings without attempting to show all the various forms and modifications in which the invention might be embodied, the invention being measured by the appended claims and not by the details of the specification.

PREFERRED EMBODIMENT FOR CARRYING OUT THE INVENTION

Figure 1:
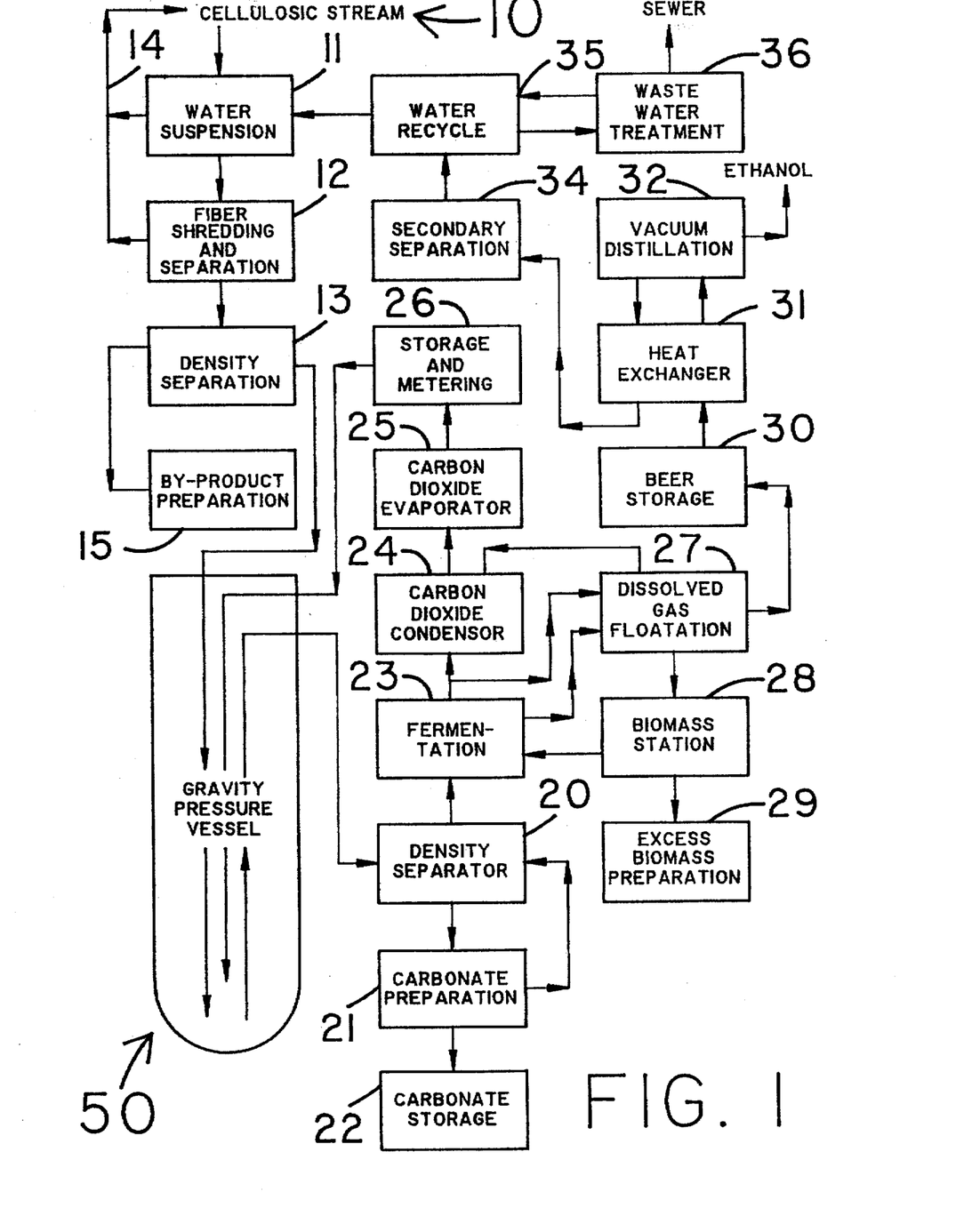
FIG. 1 is a schematic diagram of the overall process and system for producing ethanol from cellulosic material.

The overall process and system of the present invention is best described with reference to the schematic representation of FIG. 1. It should be understood, for purposes of this disclosure, particularly with regard to the schematic representation, that appropriate pumping devices and conduits are employed to move material between the various stages of the system. It should be further understood that the process which converts cellulosic material to ethanol is a continuous process, and therefore one of ordinary skill in the art will understand that various pumping devices and storage areas will be employed to maintain the process in continuous operation.

In one particular use, source material containing cellulosic material is typically obtained from municipal solid wastes, generally after the extraction of marketable goods. Source material, however, can be obtained from any of a number of sources, including but not limited to waste pulp from paper factories, spent cellulose from paper recycle plants, and refuse from food processing plants. The material obtained from municipal solid wastes is commonly referred to as residual fluff and generally includes paper scraps, lawn wastes, newsprint and cardboard, packaging wastes, wood, and food wastes which are usually rich in cellulosic content. Commonly, persons with such materials will pay for its removal.

Source material is delivered from source stream 10 to a water suspension tank 11 where water is introduced. With the introduction of water, some of the cellulosic material dissolves while some simply forms a suspension in the water, or an aqueous slurry. This mixture will be referred to hereinafter as the liquid stream. Within suspension tank 11, styrofoam and heavy materials are separated and returned to the source stream via 14.

From the water suspension tank 11, the liquid stream is delivered to a fiber shredding station 12 where solids are reduced to a common small size. When dealing with municipal solid wastes, it is specifically desirable to shred the solid underwater to preclude explosion of hazardous materials. This also allows a second opportunity to remove undesirable materials that were attached to the cellulosic material in the liquid stream. The shredding station 12 may also be adapted to separate very dense materials, such as steel bottle caps, as well as light materials such as a styrofoam. These undesirable materials are also returned to the source stream via 14.

The liquid stream is then received by a density separator 13, such as a clarifier, where gravity separation allows for the separation of supernatant materials lighter than water. Such supernatant materials typically include polyethylene plastics, styrofoam and the like, which are floated to the top and removed for further processing which can include pelletization such as at by-product preparation stage 15. Heavier subnatent materials, mostly cellulosic material, remain in the liquid stream. For purposes of this disclosure, the steps described above will generally be referred to as processing the cellulosic material into a liquid stream.

The processed liquid stream is then introduced to a gravity pressure vessel 50 for hydrolyzing cellulosic material. For example, when municipal solid wastes are employed, the liquid stream delivered from the shredding station 12 typically includes about five percent solids, and following density separation at 13 the liquid stream is concentrated to about nine percent or more suspended solids.

Within the gravity pressure vessel 50, which will hereinafter be described in more detail, the liquid stream is subjected to proper conditions for carrying out acid hydrolysis. This hydrolysis converts a significant portion of the cellulosic materials to sugars. It should be appreciated that the resulting sugars become part of the liquid stream following hydrolysis. For purposes of this description, the term sugars will generally refer to those products resulting from the acid hydrolysis of cellulosic materials, typically definable as sugars and starches and derivatives thereof. It should be appreciated, however, that a very broad spectrum of resultant materials may result from hydrolysis, even when closely controlled feed stocks are employed. Thus, when viewed in light of the fact that a source stream of the present invention could include more than 10,000 identifiable materials, many forms of sugars or starches are possible. When converting municipal solids wastes, the acid hydrolysis will yield a weak solution containing approximately 3.5 percent to approximately 5 percent sugar, which will produce a weak beer in fermentation.

The liquid stream, now containing an aqueous sugar solution, is delivered to a post treatment clarifier, such as density separator 20. Within this clarifier, heavy refractory cellulose, lime, gypsum and inert precipitates are removed. These materials are forwarded to a dewatering or carbonate preparation process 21 where the water, which contains sugar, is removed and returned to the liquid stream at separator 20. The solids, which can generally be defined as carbonates with some sulfates and mud, are stored at carbonate storage 22 for future commercial use.

The aqueous sugar solution, which also contains residual particles of unreacted cellulose, is delivered from separator 20 to a fermentation apparatus 23, which typically includes several tanks. Not shown are certain heat exchangers that may be necessary to precondition the aqueous sugar stream. This preconditioning generally includes extracting furfural and other fermentation inhibitors known to those skilled in the art. Fermentation at apparatus 23 generally involves the introduction of conventional beer yeasts, and the maintenance of active moderate agitation, atmospheric pressure, and a temperature in the range of about 70° F. to about 100° F. Maximum ethanol yield typically occurs within the time duration of about 24 to about 36 hours, with variations in time, as well as temperature, depending on the selection of yeast and other stimulating additives such as enzymes.

The products of fermentation are ethanol and carbon dioxide, produced in 1:1 ratio as generally understood by those skilled in the art. The carbon dioxide is captured from fermentation apparatus 23 and directed to a cleaning station 24, such as a condensor. Here, the carbon dioxide can be condensed under pressure and cooled for purification. The purified liquid carbon dioxide is delivered to an evaporator 25 and stored at a metering station 26 for future use in the hydrolysis of the cellulosic material at gravity pressure vessel 50, or elsewhere in the process as needed. Generally, when municipal solid wastes are employed as source material, about 80 percent of the acidification needs for hydrolysis are satisfied using carbon dioxide produced during fermentation.

Because the fermentation of the sugar took place in an aqueous solution, commonly referred to as beer, the resulting ethanol remains in aqueous solution. This beer is delivered to a dissolved gas floatation station 27. Here, particulate impurities suspended in the solution are removed. These impurities include, but are not limited to, living organisms, dust, yeast and cellulose. Removal of such particulate impurities typically includes dissolving the carbon dioxide, or any gas such as air, in water under pressure. This solution is flash mixed with the beer in an atmospheric tank. As the dissolved carbon dioxide precipitates from the mixture, it attaches to nucleic bubble formation on the surface of the suspended solids. The combined bubble and suspended solid, now lighter than water, is floated to the surface.

The separated particles are conveyed to a biomass recycle station 28 where the yeast is tested and verified for seeding the fermentation process, and the remainder conveyed to an excess biomass preparation station 29 for conventional dewatering and shipment as a protein supplement for animal feed. The remaining liquid from the dewatering process is returned to the liquid stream.

The purified aqueous ethanol solution, or beer, is delivered to a beer storage station 30. When distillation of the ethanol is desired, the solution may be pre-heated by a heat exchanger 31 and then received by a vacuum distillation column or columns 32. This can be any form of distillation and typically requires external heat from a source such as steam. After primary distillation at columns 32, the distillate is transferred to a secondary separation apparatus 34 where residual organics are typically removed. Apparatus 34 could include, but is not limited to, engineered zeolite, reverse osmosis, or extraction and concentration using ice crystallization. It has been found that the use of evaporation to accomplish this secondary separation is far too mechanically and energy intensive to be economical or efficient.

The distillate is ethanol that is approximately about 95% to about 99% pure, or greater than 193 proof as commonly understood in the art. Further, the distillate can be dehydrated to achieve 199.5 proof. This distillate is cooled and delivered to either an awaiting transport vehicle or storage tank. The spent aqueous solution, on the other hand, is cooled and delivered a recycle station 35. It should be noted that the cooling of both the purified ethanol and the spent aqueous solution can occur within a heat exchanger, such as 31, which is preferably a counterflow heat exchanger. Thus, heat from distillation process 32 is used to preheat the fluid stream of ethanol, i.e. beer, prior to distillation.

At recycle station 35, the spent water is tested. Based on the quality of the water, the spent aqueous solution is recycled back to the system to suspend incoming cellulosic material at water suspension tank 11, or treated at an on-site waste water treatment plant 36. After treatment at 36, the water may be diverted to a publicly owned treatment works or used at tank 11. The treatment plant 36 should be capable of processing 72,000 gallons per day, with a net water discharge to the publicly owned treatment works preferably as low as 10,000 gallons per day.

On-site treatment plant 36 can include a conventional waste activated solids extended aeration biological waste water treatment plant wherein excess nitrates are removed prior to discharge to a publicly owned treatment works.

As previously described, the liquid stream of cellulosic material is hydrolyzed in gravity pressure vessel 50. This apparatus is best described with reference to FIGS. 2 & 3. A tubular casing 52 is positioned in the strata S in a bore within the earth. Casing 52 can be separated from strata S with a grout to control the intermixing of fluids that may be present in the strata, to reduce the heat losses from the apparatus, and to protect the casing 52 from adverse corrosive effects of strata S. Optionally, a surface casing 51 may be employed, which is an additional tubular member encompassing strata casing 52 for the purpose of protecting water aquifers during drilling of the long string chamber bore hole.

Figure 2:
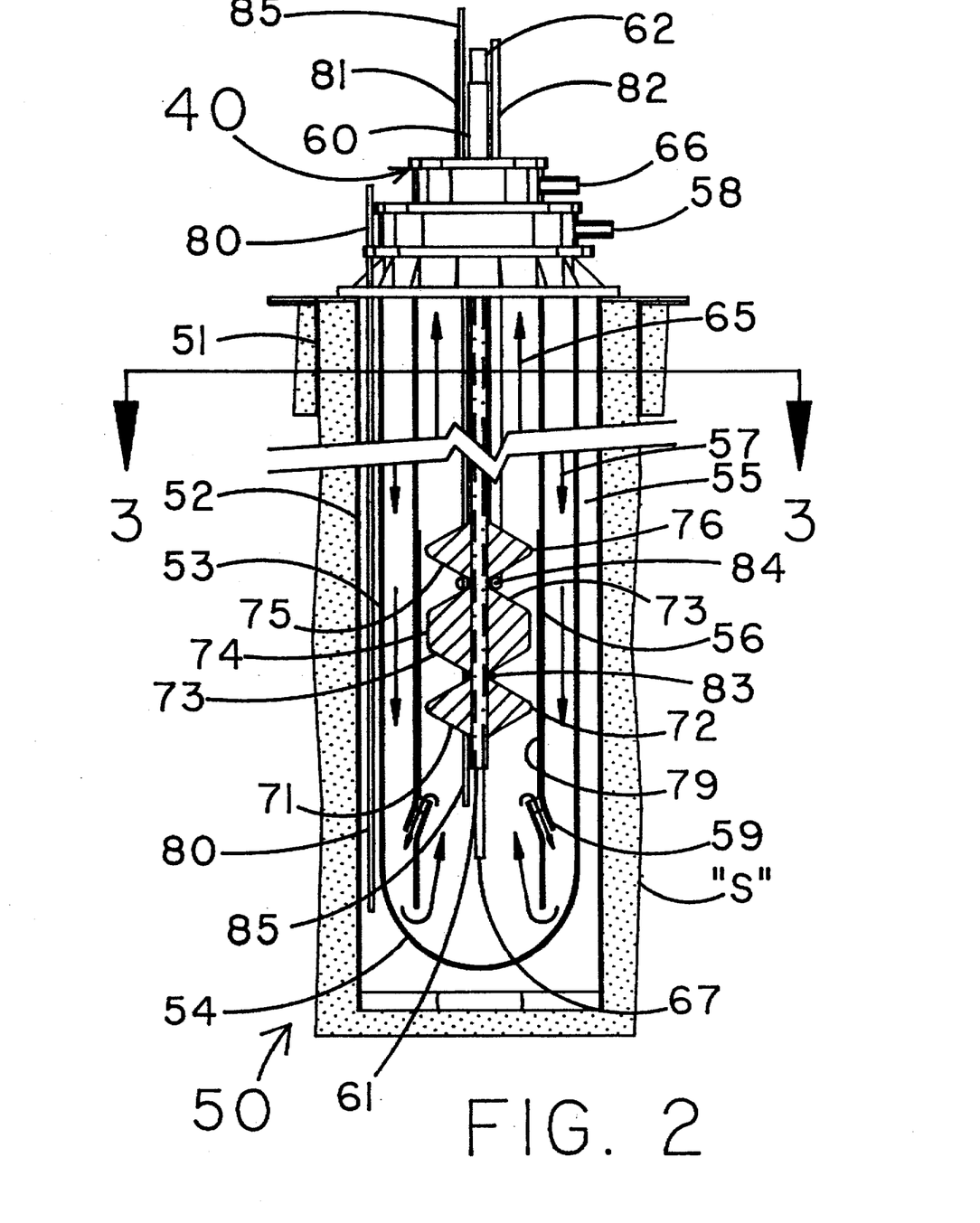
FIG. 2 is a fragmented vertical, cross-sectional view of a gravity pressure vessel in place within the strata.
Figure 3:
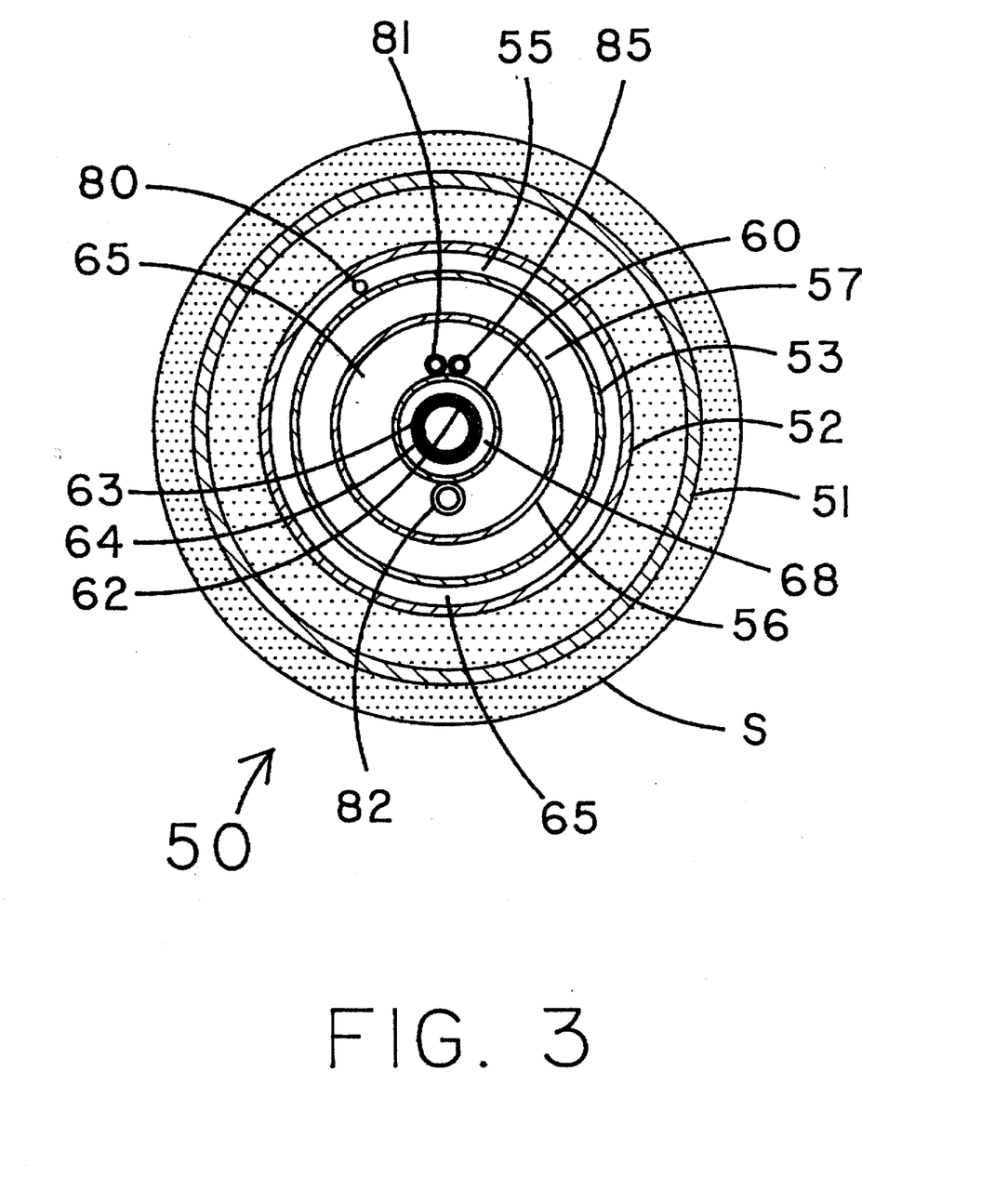
FIG. 3 is a sectional view taken substantially along line 3—3 of FIG. 2.

Concentric within and spaced from casing 52 is an outer reactor tubular casing 53 having lower closed end 54. The space between casings 52 and 53 forms an isolating annulus 55 that acts as a mutual barrier to protect the strata from the process and to protect the process from the strata. Such isolation may be enhanced by evacuating annulus 55 to a lower pressure, such as to approximately one thousandth of an atmosphere. Under such conditions, the integrity of casings 52 and 53 will be verified and heat loss to the strata from the apparatus will be greatly reduced, as will the corrosive effects on the surfaces of both casing 52 and outer reactor casing 53. A closed and sealed drop tube 80 can be positioned in annulus 55 to house thermocouples to monitor temperature conditions within annulus 55, as well as within the outer reactor casing 52.

Concentric within and spaced from the outer reactor casing 53 is counterflow tubular casing 56. The space between outer reactor casing 52 and counterflow casing 56 forms outer reactor annulus 57. The liquid stream containing cellulosic material, which enters the apparatus at inlet 58, is caused to descend to a zone of higher pressure within outer reactor annulus 57. This pressure results from the cumulative weight of the fluid, as well as from residual pressures from fluid handling pumps. Thus, annulus 57 essentially is a vertical passageway or hydraulic downdraft column that receives the liquid stream and delivers the stream to the bottom of gravity pressure vessel 50. The bottom of counterflow casing 56 can be modified with an outward flare 59 to assist the induction of recirculation of the liquid stream near the bottom of annulus 57, and produce a more uniform feed as the liquid moves through the reaction vessel.

As is best shown in FIG. 3, concentric within and spaced from the counterflow casing 56 is carbon dioxide input tube 60 which essentially is a means for delivering gaseous material to the bottom of vessel 50 via carbon dioxide annulus 68. Carbon dioxide is delivered to the lower closed end 54 of reaction vessel 50 through input tube 60 from its discharge point at 61 as shown in FIG. 2.

Referring again to FIG. 3, concentric within and spaced from input tube 60 is a tubular steam pipe 62 which represents a means for delivering heat to the bottom of vessel 50. Steam pipe 62 is concentrically nested within an outer tubular housing 63, whereby steam pipe 62 and outer housing 63 form annulus 64 which may be insulated or evacuated to prevent the premature loss of heat from steam pipe 62. Steam pipe 62 delivers heat energy, on an as needed basis, to the reactor vessel 50 from its discharge point at 67 to the region generally defined by the lower closed end 54 as shown in FIG. 2.

The space between carbon dioxide input tube 60 and counterflow casing 56 forms inner reactor annulus 65, which defines a second vertical passageway or hydraulic updraft column. The liquid stream containing cellulosic material, which descends down outer annulus 57, subsequently ascends up inner annulus 65 and out of the reactor vessel 50 through outlet 66. The forces driving this ascension, as well as the reactions taking place to the cellulosic material as it ascends, will be described in greater detail hereinafter.

As is best depicted in FIG. 2, the gravity pressure vessel is capped with device 40. Generally device 40 will serve to seal the annuli of reactor vessel 50 from the atmosphere, thereby maintaining the desired pressure or vacuum. As is generally shown, device 40 can be equipped with the inlet 58 and the outlet 66 previously described, although those of ordinary skill in the art will be able to modify the device 40, based on the teachings herein. Of course, device 40 is able to accommodate various feed pipes and housings for analytical devices, which will both be described hereinafter and which one or ordinary skill may find necessary to achieve the objects of this invention based on the teachings herein.

To a portion of the vertical length of carbon dioxide input tube 60 there is removably attached an inner reactor casing generally indicated by the numeral 70. More specifically, inner reactor casing 70 is removably attached to and circumscribes a portion of input tube 60. It should be appreciated that, with inner reactor casing 70 attached to tube 60, the shape of annulus 65 is modified. This modified area of annulus 65 essentially creates and defines a reaction area.

Inner reactor casing as generally indicated by the numeral 70 is best described with reference to FIG. 4. In the preferred embodiment, inner reactor casing 70 generally includes three venturi sections that are positioned along the same vertical axis with respect to the length of the carbon dioxide input tube 60. The first venturi section 71 generally includes two oppositely directed frustums connected at their bases, which circumscribe the carbon dioxide input tube 60. As a result of this configuration, the inner annulus 65 is reduced at the junction of the two bases 72.

The second venturi section 73, which is positioned above and connected to the first venturi section 71, generally includes two oppositely directed frustums having a generally cylindrically shaped member 74 connected therebetween. Cylindrical member 74 preferably has the same diameter as the bases of the frustums, and the bases of each frustum are connected to member 74. The frustums and the cylindrical member circumscribe the carbon dioxide input tube 60. As a result of this configuration, the inner annulus 65 is reduced at the junction of the bases and cylindrical member, and remains reduced throughout the vertical length of member 74. As is particularly the case with member 74, the length and configuration of the inner reactor casing 70 can be modified. For example, reactor casing 70 can be removed and member 74 can be modified in length. This is typically accomplished by replacing it with a longer member or by simply adding additional members, similar to 74, between the frustums of the second venturi section. In turn, lengthening member 74 will increase the length of the reduced portion of annulus 65.

The third venturi section 75, which is positioned above and connected to the second venturi section 73, generally includes two oppositely directed frustums connected at their bases 76. The frustums circumscribe the carbon dioxide input tube 60. As a result of this configuration, the inner annulus 65 is reduced at the junction of the two bases 76.

It should be understood that while the inner reactor casing has been described with reference to the preferred embodiment, the inner reactor casing can be any means that serves to reduce and expand the width of inner annulus 65 in a manner generally consistent with that described in the preferred embodiment. Specifically, based on the teachings herein, one skilled in the art should be able to design numerous configurations that serve to alter the flow rate of fluid as it travels up annulus 65.

Figure 4:
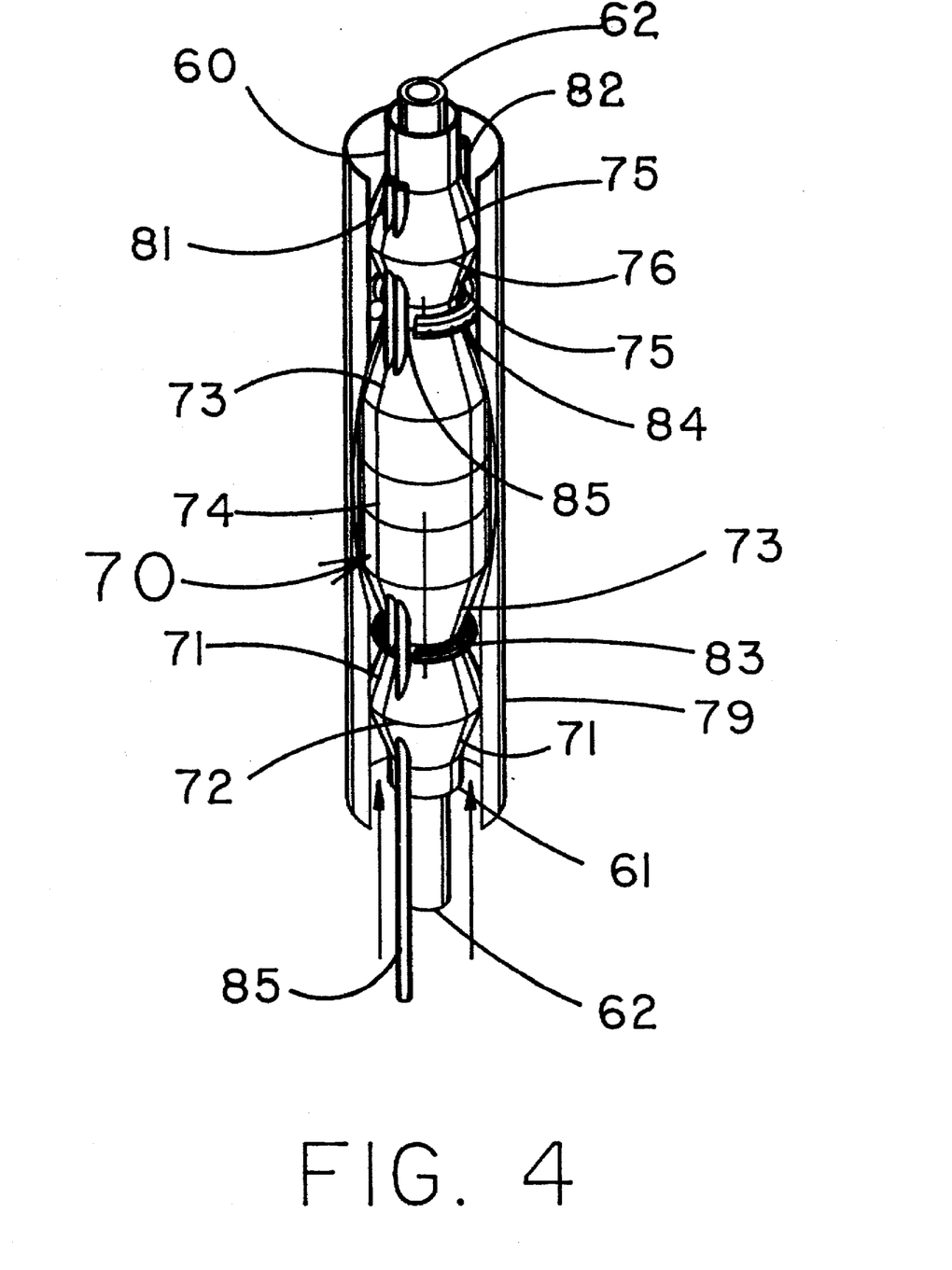
FIG. 4 is an isometric view of a portion of the gravity pressure vessel exposing the inner reactor casing.

Also represented in FIG. 4 are an acid feed pipe 81 and a caustic feed pipe 82. In the preferred embodiment, acid feed pipe 81 supplies acid to an acid feed collar 83, which is generally positioned at the junction of first and second venturi sections. From acid feed collar 83, acid can be dispersed throughout inner annulus 65 in the region generally adjacent to feed collar 83. Caustic feed pipe 82 supplies caustic to a caustic feed collar 84, which is generally positioned at the junction of second and third venturi sections. From caustic feed collar 84, caustic solution can be dispersed throughout inner annulus 65 in the region generally adjacent to feed collar 84. It should be understood that any means of delivering acid and caustic to the above defined regions can be employed for purposes of this invention. Further shown in FIG. 4 is thermocouple tubular housing 85, which may be employed to monitor the physical and chemical characteristics of the continuously flowing fluids within reactor vessel 50.

The apparatus as just described is highly useful to perform the process of converting cellulosic material to sugars for the subsequent conversion to ethanol. As previously described, the term sugars is generally meant to refer to those products resulting from the acid hydrolysis of cellulosic materials. This conversion occurs via chemical reactions taking place within vessel 50 as cellulosic material, dissolved or mixed within an aqueous stream, continuously flows through the vessel.

The hydrolysis of cellulosic material is now best described with reference to FIG. 5. Steam, which is pumped down steam pipe 62, is introduced to the process and heats the stream of fluid in the region 90, generally defined as that region near the lower closed end 54 of reactor casing 53. Moreover, once the vessel is in continuous operation, heat resulting from acid hydrolysis reactions taking place in reaction regions 92 and 93, as will later be explained, migrates through counterflow casing 56 to heat the fluid stream as it descends down outer reactor annulus 57. Thus, steam from pipe 62 is delivered only on an as needed basis; that is, to compensate for that portion of downflowing fluids insufficiently preheated though counterflow 56. It is noteworthy that a maximum amount of heat energy can be recaptured by introducing the steam in the region 90.

It should be appreciated that the heat needed to drive a hydrolysis reaction of cellulosic material is generally greater than 200° C. and preferably in the range between about 260° C. and about 290° C. The greater the temperature, the less acid is needed to drive the reaction. At too great a temperature, however, the hydrolysis reaction is not easily controlled, and, therefore, results in the decomposition of the sugar product. Thus, based on the teachings herein, one of ordinary skill in the art will be able to alter the temperature and acidity level to achieve optional results. Of course, the constantly changing feed stream will also factor into the optimal temperature and acidity sought. It should further be appreciated that the pressure experienced by the liquid stream within the gravity pressure vessel increases as the liquid stream approaches the bottom of the vessel. This increased pressure, which is generally in the range of between about 600 psi and about 1200 psi, and preferably between about 800 psi and about 1000 psi, further serves to drive the hydrolysis reaction.

Because of the pressure resulting from the height of the liquid stream descending down outer reactor annulus 57, and the reduction in the density of the fluid resulting from the introduction of carbon dioxide, the liquid stream is caused to ascend up inner reactor annulus 65, a portion of which has been modified to define a reaction area as described hereinabove. For purposes of explaining the hydrolysis of the cellulosic material ascending up through the reaction area, the reaction area will be defined in terms of six regions. The first region 91 is generally defined as that region of annulus 65 below point 72 of first venturi section 71. At or near first reaction region 91 is the area where carbon dioxide input tube 60 terminates at 61, thereby introducing the carbon dioxide to the liquid stream in region 91. It should also be noted that the carbon dioxide is preheated prior to its entry in the process as a result of steam pipe 62 being concentric and within carbon dioxide input tube 60. The carbon dioxide forms carbonic acid within the liquid stream thereby lowering the pH and catalyzing the hydrolysis reaction. It is preferred that enough carbon dioxide be added to the liquid stream to bring the pH of the solution below 5.0 and preferably below 3.5.

The preheated liquid stream, now containing sufficient carbon dioxide, continues to ascend up annulus 65 and encounters the second reaction region 92 where the flow of the fluid stream is restricted due to first venturi section 71. The liquid stream's contact with venturi section 71 creates a minor shock wave in the passing fluid that is a source of instantaneous mixing of the fluid and suspended particles.

Moving upward through annulus 65, the fluid stream next enters third reaction region 93. Region 93 is generally defined as the area within annulus 65 adjacent to or near the junction of first venturi section 71 and second venturi section 73. Within region 93, acid is introduced to the system from a device such as acid feed collar 83, to achieve a pH in the range of about 2.0 to about 3.0, which carries out hydrolysis of the cellulosic materials. While it is believed that any mineral acid will serve to lower the pH as sought in the present invention, sulfuric acid has been found to work particularly well and is preferred. It is noteworthy that such acid is only needed when the pH is insufficiently lowered by the introduction of carbon dioxide to the liquid stream.

As acid hydrolysis reactions convert the cellulosic material to sugars, the fluid stream continues up annulus 65 and enters forth reaction region 94. Region 94 is generally defined as the area within annulus 65 adjacent to and reduced as a result of cylindrical member 74 of second venturi section 73. Region 94 is restricted to increase the flow rate of the fluid stream undergoing acid hydrolysis, thereby limiting the time in which hydrolysis takes place. As previously described, extended acid hydrolysis of the cellulosic material beyond the required time will destroy the sugars that are sought from the reaction. Typically, it will take about 2 to about 4 seconds for the fluid stream to ascend through region 94. Because the reaction time is critical and may vary on several factors including the nature of the feed stock, the length of region 94, and therefore the reaction time, can be changed. This is accomplished by adding or removing sections of tube 74 as was described hereinabove.

Moving rapidly through region 94, the fluid stream then ascends into the fifth reaction region 95. Region 95 is generally defined as the area within annulus 65 adjacent to or near the junction of second venturi section 73 and third venturi section 75. Within region 95, caustic solution, such as calcium hydroxide, is introduced via a device such as caustic feed collar 84. The introduction of caustic solution raises the pH to approximately 7.5 or greater, thereby quenching the acid hydrolysis reaction. The introduction of a neutralizing agent such as calcium hydroxide further results in the formation of precipitants such as calcium carbonate and calcium sulfate. To prevent the fouling of the annuli walls, seed powders of these precipitates can be added with the caustic solution to the stream, causing the formation of larger precipitate particles that can be later removed. It should be understood that any caustic solution can be introduced which will neutralize the stream of liquid, thereby quenching the hydrolysis reaction, so long as such caustic solution is not deleterious to the sugar product or liquid stream.

Ascending toward the top of reactor vessel 50, the fluid stream is again restricted in sixth reaction region 96 due to third venturi section 75 is which creates shock wave mixing. Continuing to move upward from this region, the fluid ascends unrestricted up the remainder of annulus 65 and eventually reaches the top of the reactor vessel 50 where it exits the vessel at outlet 66.

As should be evident to one of ordinary skill in the art, the reaction time is a function of the rate of flow of the liquid stream through vessel 50. In other words, the reaction time is dictated by the time it takes the stream to move through the reaction area. Generally, the stream will pass through the reaction area within about 3 seconds to about 6 seconds.

It should be appreciated that the quenching of the hydrolysis reaction is achieved solely by the neutralization of the fluid stream. Thus, the heat introduced at the bottom of the reaction vessel at region 90 remains in the fluid or migrates through casing 56 and heats the downward flowing input stream. It should further be appreciated that as the fluid ascends unrestricted up the remainder of annulus 65 toward the top and the reactor vessel 50, at least 80 percent, and more preferably 90–95 percent of the heat introduced via the steam at or near region 90 is captured, i.e., migrates through casing 56, or into one of the various feed pipes. In other words, the heat introduced to the reaction vessel is recycled within the gravity pressure vessel.

Figure 5:
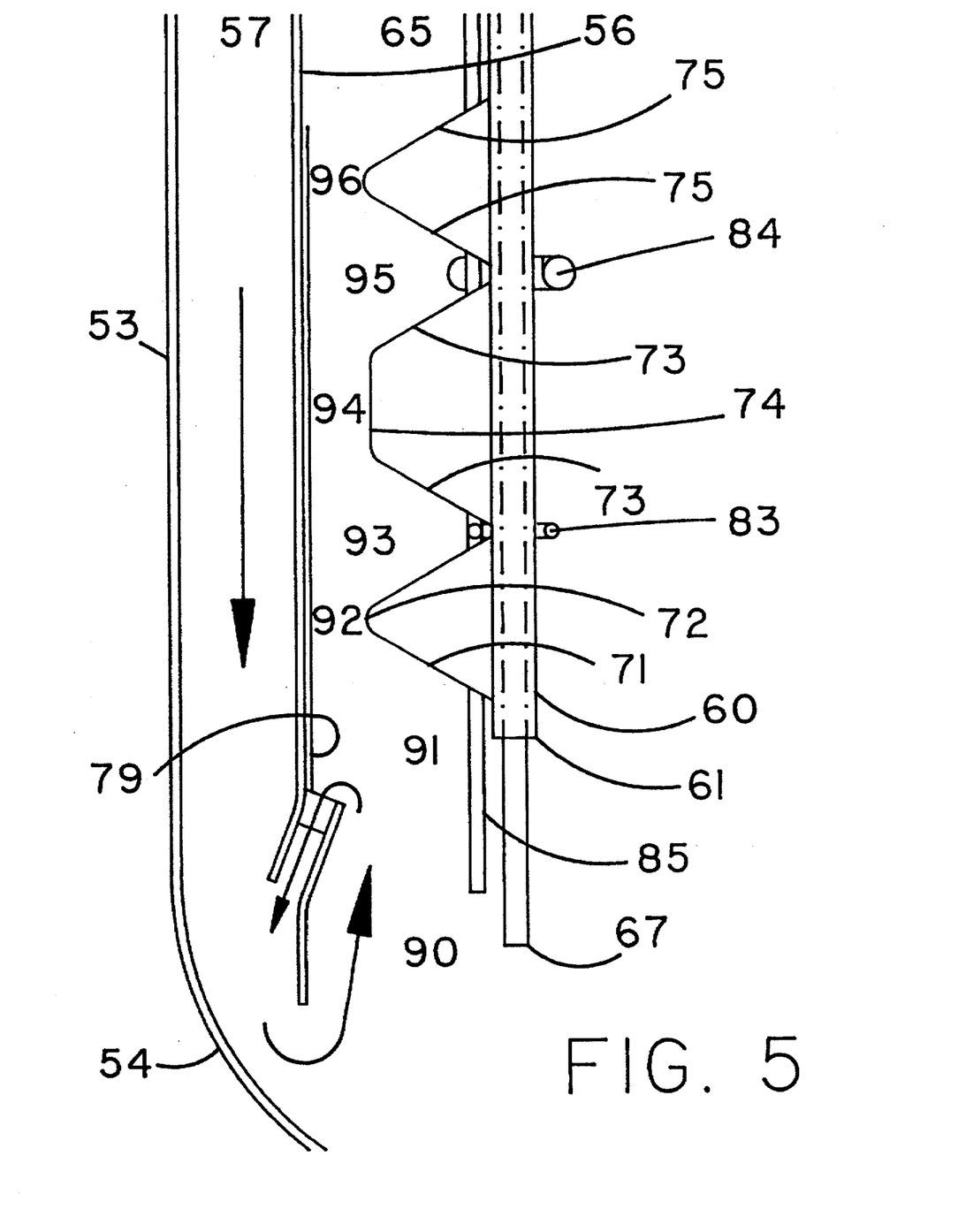
FIG. 5 is an enlarged vertical, sectional view of the gravity pressure vessel particularly showing the reaction area.

Also depicted in FIG. 5, counterflow casing 56 can be fitted with a liner 79. Although casing 56 has mechanical strength, liner 79 is relied on for resistance from chemical attack and erosional complications.

Figure 6:
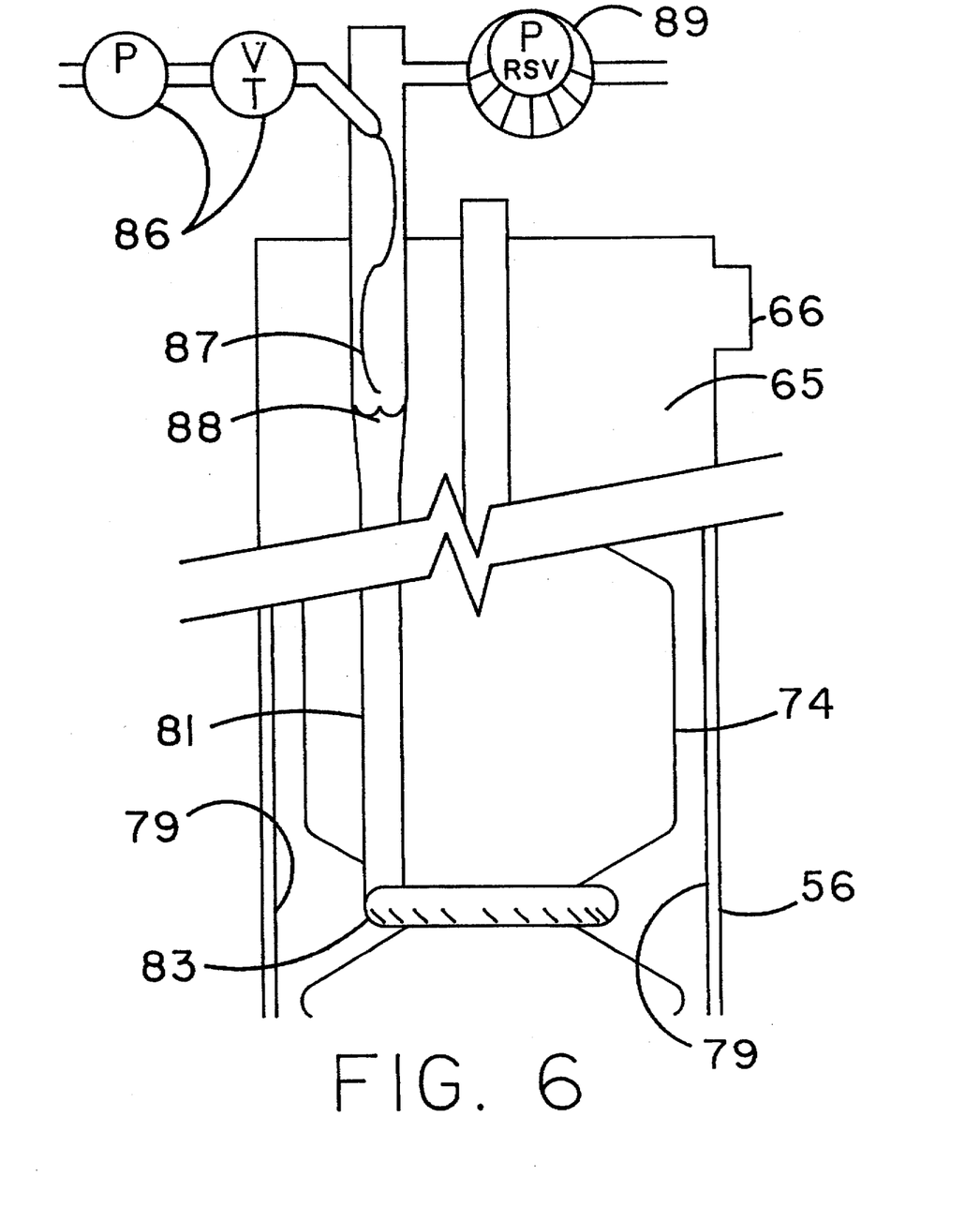
FIG. 6 is a fragmented vertical sectional representation illustrating a device for inhibiting the excessive feed of a higher density fluid into the gravity pressure vessel.

Referring again to FIG. 4, it has been discovered that the introduction of acid through acid feed pipe 81 and feed collar 83 could be problematic because the density of the acid can be up to approximately 35 percent greater than the density of hot water and the acid feed pipe is typically about 2,000 feet long. If this weight is left to act only against the frictional forces within feed pipe 81, the flow rate of the acid will exceed the required delivery rate of acid. Thus, because the accumulated pressure at the bottom of feed pipe 81 is excessive, irregularities in the discharge of the acid into the reaction region 93 could occur. To eliminate this potential problem, it is preferred to employ an arrangement, such as illustrated in FIG. 6.

This arrangement will be referred to as a vacuum compensated feed. Generally, this arrangement includes acid feed pipe 81 modified with at least one taper 88, such that the diameter of the acid feed pipe is smaller below the taper than above the taper.

The rate of acid feed is controlled by pump and valving 86. The acid is admitted into acid feed pipe 81 in a downwardly tangential manner so as to form a falling film 87 that simply wets the inner surface of pipe 81.

As the acid film 87 flows downward, it will eventually flood the entire inner diameter of feed pipe 81, such as at taper 88, and create a column of acid within pipe 81 below point 88. In other words, the height of the column of acid is generally equivalent to the height of the acid feed pipe below the taper. A vacuum is drawn, using evacuation vane pump 89 on the area above the acid column not occupied by the downward flowing film 87. Thus, the pressure at the bottom of feed pipe 81 is only the weight of the acid column, typically from taper 88 down to the feed collar 83. It is, therefore, desirable to modify acid feed pipe 81 with taper 88 such that the length of acid feed pipe 81 below taper 88 will create a pressure at the bottom of acid feed pipe 81 equivalent or approximate to the pressure within annulus 65, and more specifically, reaction region 93. It should also be appreciated that the rate of acid feed can be used to manipulate the height of the acid column.

For example, when sulfuric acid is employed, about one pound per square inch for every 1.9 feet of height is achieved. Water, on the other hand, is about one pound per square inch for every 2.1 feet of height. These values were calculated after compensating for the loss of density due to fluid expansion that results from rising temperatures as the fluids move downward in the reaction vessel 50. Based on a vessel 2000 feet deep, which is typical for mild acid hydrolysis reactions, the water pressure would be approximately 952.4 psi, while that of the acid would be approximately 1,052.6 psi. This difference causes acid delivery problems which are enhanced by the fact that the acid frictional forces are less than that of the water.

To alleviate this problem, taper 88 is created so that the distance between taper 88 and feed collar 83 is 1810 feet, thereby providing for a column of acid approximately 1810 feet. Thus, approximately 190 feet of the feed pipe is maintained under vacuum.

It should be appreciated that the height and diameters of each annulus within reactor vessel 50 are not critical, so long as the height and diameters are sufficient to achieve the goals of the present invention. Namely, the height must be such that sufficient pressure is achieved at the bottom of the reactor to drive an efficient hydrolysis reaction. Further, the height must be such that sufficient travel of the up-flowing fluid is achieved so that the heat needed for the hydrolysis reaction can be recycled into the down-flowing fluids through casing 56 in an efficient manner.

The diameter of the annuli is typically a function of the make-up of the feed stream as well as the reaction sought. Typically, the diameter of the entire vessel is greater when cellulosic material is converted to sugar than in other gravity pressure vessels. As discussed herein, however, the inner annulus 65 has a reduced diameter at certain points.

A preferred gravity pressure vessel according to the present invention will have a height from about 1800 feet to about 2200 feet. The diameter of outer reactor casing 53 is preferably about 24 inches to about 30 inches, and the diameter of counterflow tubular casing 56 is preferably about 18 inches to about 24 inches.

As with the size of the reactor, the fluid throughput of the reactor is a function of the characteristics of the feedstock. Ideally, the gravity pressure vessel of the present invention will process from about 500 to about 1000 gallons per hour of fluid stream, which typically comprises from about 5 percent to about 9 percent cellulosic material.

Further details of the pretreatment and post-treatment of the fluids and the treated products of the process and other materials of construction, proportions, cleaning, corrosion and erosion control, catalysts, alternative acids, vent extraction and control of volatile organic compounds, stress strain control, expansion compensation, and the like, would all be known to one normally skilled in the art and are not described herein.

It should thus be evident that the method and apparatus disclosed herein is capable of sustaining conditions amenable to the practical hydrolysis of cellulosic materials in commercial quantities, as the energy demands involved in pressurization and heating are significantly recovered from the process stream and not lost to mechanical forces. Further, the by-products of cellulose hydrolysis are fully contained providing options for their processing and environmentally safe use or control. As such, the objects of the present invention are fully accomplished. It is, therefore, to be understood that any variation evident falls within the scope of the claimed invention and, thus, the selection of specific component elements can be determined without departing from the spirit of the invention herein disclosed and described. For example, the size of the gravity pressure may be altered, as can the position and configuration of the reaction area. Thus, the scope of the invention shall include all modifications and variations that may fall within the scope of the claims.

I claim:

1. A method of hydrolyzing cellulosic material comprising the steps of processing the cellulosic material into a continuous liquid stream, feeding the liquid stream to the top of a hydraulic downdraft column, heating the liquid stream, conducting the liquid stream from the bottom of the hydraulic downdraft column into a reaction area, lowering the pH of the liquid stream within the reaction area, thereby promoting the hydrolysis of the cellulosic material to form sugar, regulating the reaction time of the cellulosic material within the reaction area by accelerating the flow of the liquid stream through the reaction area thereby controlling the degree of hydrolysis so as to prevent the destruction of the sugar; conducting the liquid stream into a neutralization area wherein the hydrolysis of the cellulosic material is quenched thereby terminating the hydrolysis, and conducting the liquid stream containing the sugar from the neutralization area to the top of a hydraulic updraft column.

2. A method according to claim 1, further comprising the step of lowering the density of the liquid stream prior to entering the reaction area by introducing a gaseous material to the liquid stream.

3. A method according to claim 1, wherein said step of conducting the liquid stream to the top of the hydraulic updraft column further includes the step of recovering the heat introduced by conducting the heat to the liquid stream in the hydraulic downdraft column.

4. A method according to claim 1, wherein said step of lowering the pH includes the step of introducing acid into the reaction area.

* * * * *